United States Patent [19]
Harris

[11] Patent Number: 4,998,866
[45] Date of Patent: * Mar. 12, 1991

[54] PRECISION LIQUID HANDLING APPARATUS

[75] Inventor: Arthur Harris, San Mateo, Calif.

[73] Assignee: Davis Meditech, Inc., Davis, Calif.

[*] Notice: The portion of the term of this patent subsequent to Oct. 17, 2006 has been disclaimed.

[21] Appl. No.: 414,706

[22] Filed: Sep. 29, 1989

Related U.S. Application Data

[63] Continuation-in-part of Ser. No. 85,659, Aug. 17, 1987, Pat. No. 4,873,877.

[51] Int. Cl.$^5$ ............................................. F04B 19/02
[52] U.S. Cl. ..................................................... 417/460
[58] Field of Search ............ 73/863.01, 863.11, 863.14, 73/863.16, 863.17; 422/63, 64; 417/460, 462, 467, 551

[56] References Cited

U.S. PATENT DOCUMENTS

| | | | |
|---|---|---|---|
| 3,254,607 | 6/1966 | Norton | 417/460 |
| 3,615,240 | 10/1971 | Sanz | 73/864.13 |
| 3,699,766 | 10/1987 | Yamashita | 422/64 |
| 4,207,806 | 6/1980 | Bimond et al. | 416/460 |
| 4,351,799 | 9/1982 | Gross et al. | 422/64 |
| 4,543,238 | 9/1985 | Mimura et al. | 422/64 |
| 4,738,826 | 4/1988 | Harris | 73/864.62 |
| 4,873,877 | 10/1989 | Harris | 73/864.16 |

FOREIGN PATENT DOCUMENTS 407075  3/1934  United Kingdom ................ 417/460

*Primary Examiner*—Robert Raevis
*Attorney, Agent, or Firm*—James E. Brunton

[57] ABSTRACT

An improved liquid handling system for controllably dispensing, aspirating and intermixing various liquids through the use of a precision liquid metering and aspirating device having a fixed base and a rotatable fluid containing cartridge.

7 Claims, 5 Drawing Sheets

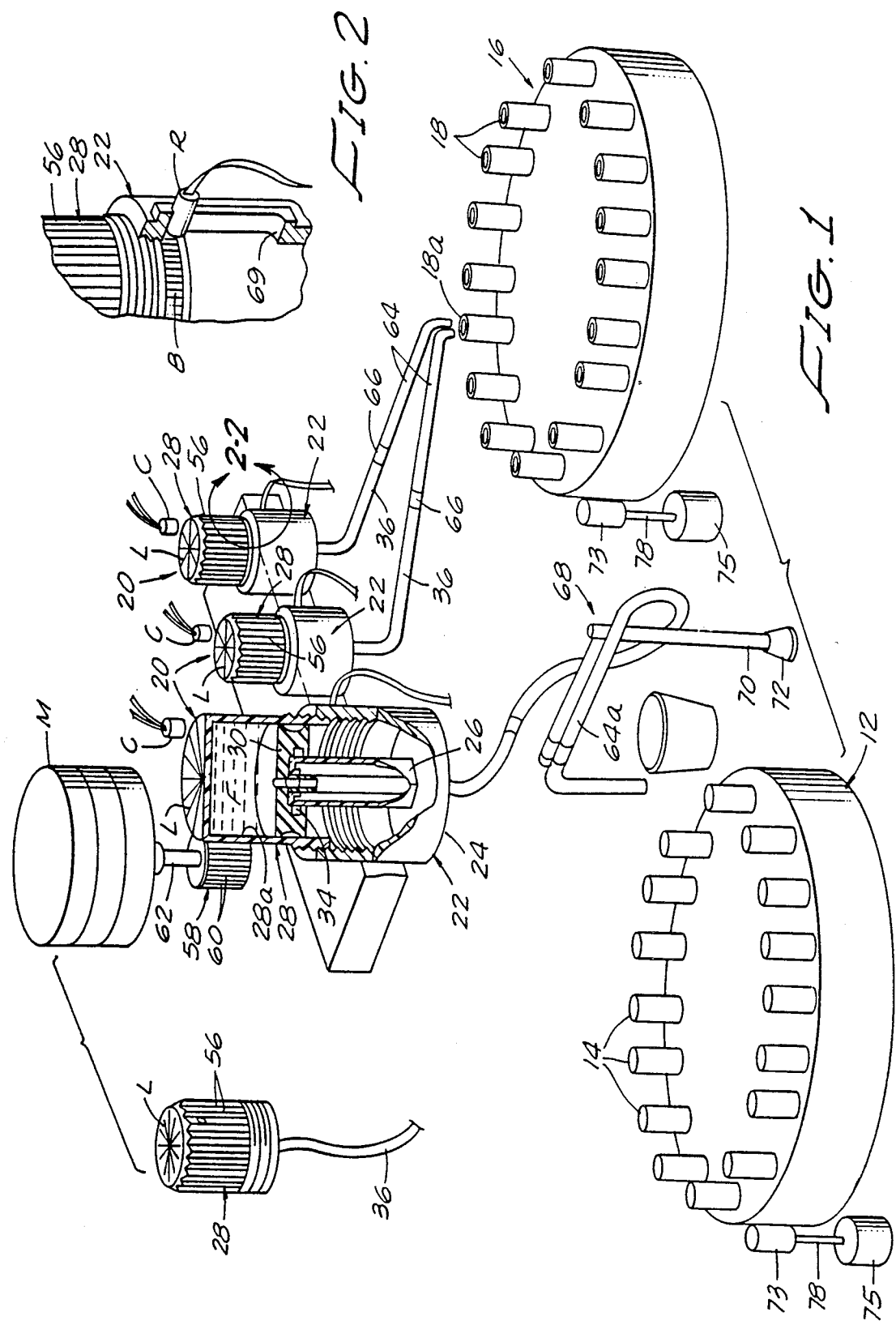

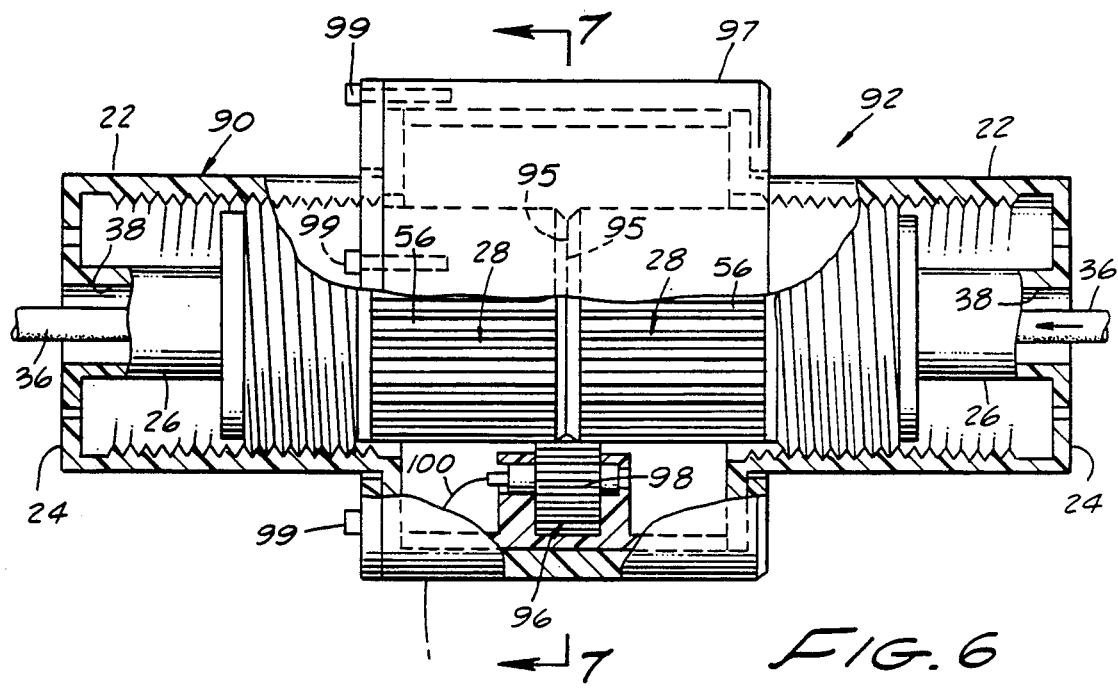
FIG. 6
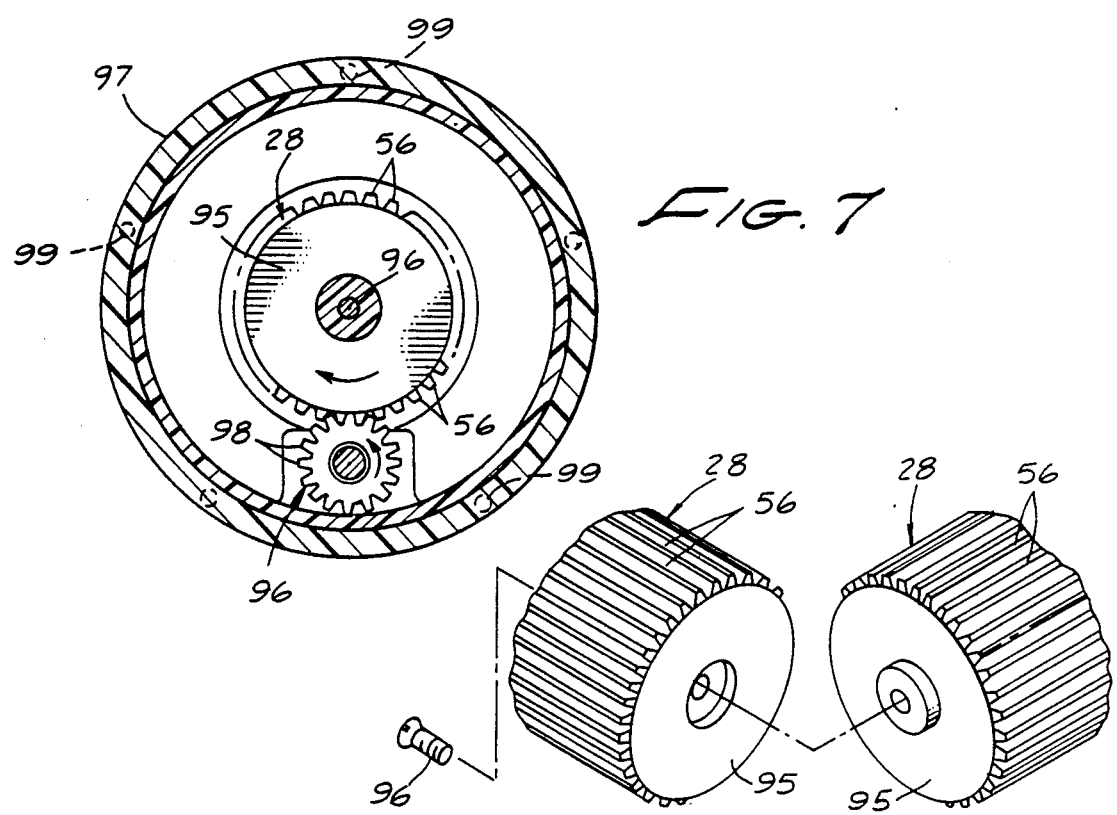
FIG. 7
FIG. 9

PRECISION LIQUID HANDLING APPARATUS

BACKGROUND OF THE INVENTION

This is a Continuation-In-Part Application of Copending Application Ser. No. 07/085,659, filed Aug. 17, 1987, now U.S. Pat. No. 4,873,877.

FIELD OF THE INVENTION

The present invention relates generally to liquid handling apparatus. More particularly the invention concerns an improved liquid handling system for controllably dispensing, aspirating and intermixing various liquids through the use of a precision liquid metering and aspirating device having a fixed base and a rotatable fluid containing cartridge.

DISCUSSION OF THE PRIOR ART

There exists in the prior art a wide variety of volumetric devices for dispensing and aspirating liquids such as reagents. On one end of the spectrum is the simple manual type, such as the pipette, wherein a quantity of liquid is sucked up into a graduated tube and then discharged as a metered quantity. On the other end of the spectrum are various highly sophisticated mechanical and electromechanical devices adapted to reproducably dispense precise quantities of liquid from conventional or specially designed reagent containers. The manual type devices often lack the necessary precision, while the mechanized devices frequently are unduly complex, extremely costly and, in many instances, tend to fail or malfunction in continuous use.

The apparatus disclosed in Garren U.S. Pat. No. 3,834,241 et al and in Valt U.S. Pat. No. 4,054,061 are exemplary of manual type pipette devices.

The apparatus disclosed in Downings U.S. Pat. No. 3,931,915 et al and in Sundstrom U.S. Pat. No. 4,101,283 are exemplary of mechanical and electromechanical dispensing devices. The latter mentioned Sundstrom device is specifically adapted for use in accurately pipetting specified digitally programmed volumes of sample and the delivery of likewise specified, digitally programmed, volumes of reagent. The thrust of the Sundstrom invention is directed toward the provision of a specially constructed plunger which is rotated within a non-threaded reagent container. Rotation of the plunger is controlled by a relatively sophisticated light-photo cell system which is operably interconnected with motor means through somewhat complex counting and connecting circuits. As a result of the particular configuration of the Sundstrom plunger, it cuts grooves in the inner wall of the reagent container as it rotates.

One of the most successful reagent metering and dispensing devices developed to date is described in the copending application Ser. No. 823,939 filed by the present inventor.

The apparatus of the present invention embodies, as a subassembly thereof, the device described in Ser. No. 823,939. As will be better understood from the description which follows, the apparatus of the present invention is extremely versatile and well suited for automatically performing liquid handling operations requiring the utmost precision. For example, the apparatus can be used for automated liquid sampling and analysis, for automated infusion of liquids to a patient via an access catheter, and for the precision mixing of liquids such as reagents, medical specimens, inks, paints and the like.

The apparatus is readily distinguishable from the prior art in that it solves the problems inherent in the precision aspiration and dispensing of large or small liquid aliquots by providing a simple, inexpensive, positive acting, and highly versatile liquid handling apparatus. Because of its simplicity, the apparatus of the present invention is easy to maintain and clean, is highly reliable in operation and can readily be operated by unskilled, non-professional personnel.

SUMMARY OF THE INVENTION

It is a primary object of the present invention to provide a simple, highly reliable and easy to operate liquid handling apparatus which can automatically aspirate, dispense and intermix various fluids with extreme precision.

More particularly, it is an objective of the present invention to provide a relatively simple easy to operate instrument designed to include a precision metering device that also functions in reverse as a sampling device. Due to the unique, simplified design of the device, high precision and accuracy in both modes of sampling and delivery can readily be realized.

It is another object of the invention to provide an apparatus of the aforementioned character in which the component parts which make up the apparatus are of clean design and can be manufactured of inexpensive, easily fabricated and readily available materials.

Still another object of the invention is to provide an apparatus of the character described in the previous paragraphs which embodies a minimum number of component parts and, therefore, is simple to clean and maintain.

A further object of the invention is to provide a device of the class described which makes use of prepackaged, disposable cartridges containing reagents or other liquids which can be readily installed by nonprofessional personnel with minimum system downtime and can then be discarded after use.

Yet another object of the invention is to provide an apparatus of the class described which permits simple rotational control of the liquid containing cartridge of the liquid metering and aspirating device with relation to the stator member thereof through the use of an encoder reader or other digital control device, such as an optical or magnetic device, which provides precision control over both liquid dispensing and liquid aspirating by directly sensing the rotational movement of the liquid containing cartridge thereby eliminating all effects of backlash or slippage due to mechanical linkages.

Another object of the invention is to provide an apparatus of the character described which can be used as a reagent or therapeutic delivery system wherein the individual fluid filled cartridges can be individually programmed with precision to deliver on demand and in proper sequence, liquids either in a liquid dispensing or liquid sampling (withdrawal) mode.

Still another object of the invention is to provide an apparatus as described which can be used as a precision infusion device for fluid infusion to a patient via an access catheter.

BRIEF DESCRIPTION OF THE DRAWINGS

FIG. 1 is a generally perspective view of one embodiment of the liquid handling apparatus of the invention. Portions of the apparatus are enlarged, exploded and shown partially in cross section to better illustrate the construction of the liquid metering and aspirating devices of the apparatus of the invention.

FIG. 2 is an enlarged fragmentary view, partially in cross section, taken along lines 2—2 of FIG. 1 showing the encoder reader of the liquid metering and aspirating device used to identify the contents of the container and to instruct an ancillary computer system.

FIG. 6 is a cross sectional view of still another embodiment of the invention.

FIG. 7 is a cross-sectional view taken along lines 7—7 of FIG. 6.

FIG. 9 is a fragmentary, generally perspective view of portions of the reagent containers illustrating the method of interconnection thereof.

DESCRIPTION OF THE INVENTION

Figure 3:
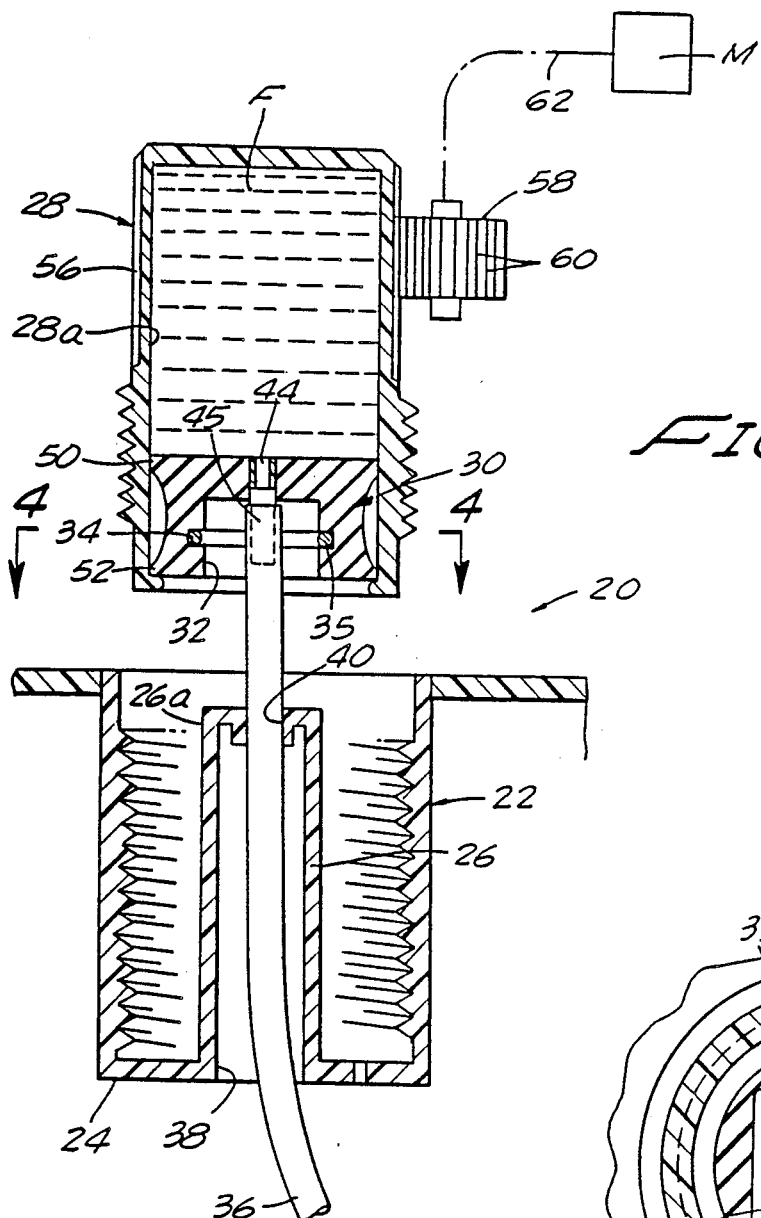
FIG. 3 is an exploded side elevational cross sectional view of one form of the liquid metering and aspirating device of the present invention.
Figure 4:
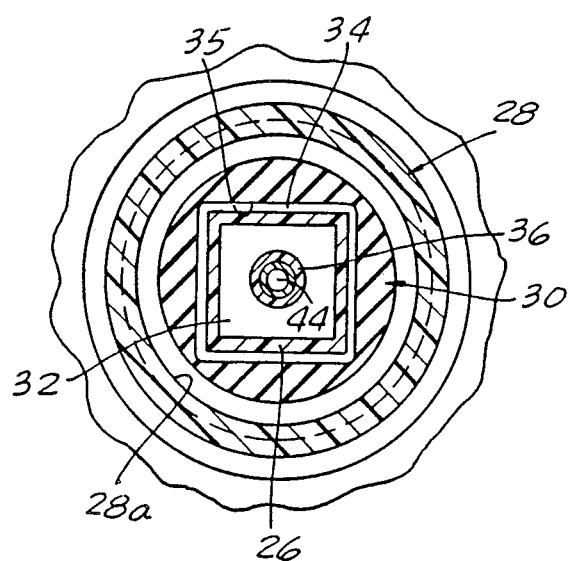
FIG. 4 is a cross sectional view taken along lines 4—4 of FIG. 3.

Referring to the drawings and particularly to FIGS. 1 and 2, one embodiment of the liquid handling apparatus of the present invention is there illustrated. The apparatus comprises a first rotatable carousel 12 for carrying a plurality of first liquid reservoirs 14, a second rotatable carousel 16 for carrying a plurality of second liquid reservoirs 18 and three liquid metering and aspirating devices 20 which are operably associated with the liquid reservoirs carried by carousels 12 and 16 via first and second transfer means the details of which will presently be described.

Each of the liquid metering and aspirating devices of this form of the invention comprises an internally threaded hollow base member 22 having a bottom closure wall 24, a rigid stator, or upstanding hollow column, 26 mounted within base member 22 and an externally threaded liquid container, or disposable cartridge, 28 adapted to be threadably interconnected with base member 22 upon rotation of container 28 relative to base member 22. Each of the liquid metering and aspirating devices of the invention further includes a liquid delivery means for conducting fluid from the interior of the liquid container 28 to the exterior of the device and a non-rotatable plunger 30 reciprocatable movable a precise axial distance with respect to liquid container 28 upon rotation of the container 28 relative to the base member 22.

The plungers 30 of the liquid metering and aspirating devices each have sealing means adapted to sealably engage the inner wall 28a of the liquid container 28 for preventing leakage of fluid between the plunger and the inner wall of the container upon non-rotatable axial movement of the plunger 30 within the liquid container 28. Plunger 30 is also provided with connecting means for operably interconnecting the plunger with the stator 26 for preventing rotation of the plunger relative to the stator. Additionally, the plunger includes releasable locking means for releasably interconnecting the plunger with the stator to prevent relative axial movement therebetween during the aspirating mode of operation of the device.

In the embodiment of the invention shown in the drawings, the connecting means of each liquid metering and aspirating device is provided in the form of a cavity 32 which, as shown in FIG. 3, is generally rectangular in cross-section and is adapted to closely receive the upper end portion of the stator, or upstanding column, 26. The interlocking means in this form of the invention comprises a resiliently deformable locking member 34, such as a molded detent or a thin metal spring or wire, which is receivable within a circumferentially extending groove 35 formed in cavity 32 of plunger 30. As will be discussed in greater detail hereinafter, when container 28 is rotated relative to base 22, the upper portion of stator 26 will be closely received within cavity 32. As this occurs, the resiliently deformable locking member 34 will frictionally engage and securely grip the side walls of stator, or column 26, thereby yieldably resisting relative axial or rotational movement between the plunger 30 and the stator 26.

In each of the liquid metering and aspirating devices of the apparatus, is provided in the form of a tubular conduit 36 (FIG. 3) which extends through an aperture 38 formed in bottom wall of base 24. The conduit then extends through hollow column 26 and then outwardly through an aperture 40 formed in the upper portion 26a of stator 26. Plunger 30 is provided with a fluid passageway 44 having one end communicating with the interior of the liquid container 28 and the other end communicating with the first, end 45 of conduit 36.

In the present embodiment of the invention, the previously identified sealing means of each liquid dispensing and aspirating device comprises a pair of spaced apart circumferentially extending skirts 50 and 52, the outer edges of which press resiliently against the inner wall 28a of container 28. While sealing skirts are shown in the drawings, it is to be understood that conventional type elastometric O-rings could also be used as the sealing means.

The drive means of this form of the invention comprises a multiplicity of splines 56 provided about the periphery of each of the liquid containers, or cartridges, 90 and 92. A drive roller 96, also having a multiplicity of splines 98 provided about its periphery, is adapted to mateably engage and controllably drive the pair of reagent containers 90 and 92. A motor means M is operably connected with drive roller 96 by a suitable driving connection 100. The details of the operation of the drive and control means of the present form of the invention will be discussed in greater detail in the paragraphs which follow describing the operation of the apparatus of the invention.

When the parts of the liquid dispensing and aspirating devices of the apparatus are mated in the manner shown in the exploded portion of FIG. 1, rotation of reagent container 28 relative to the base 22 will cause the reagent container to travel downwardly in relation to plunger 30, which is fixed against rotation by the stator. Since the sealing means, or skirts 50 and 52, provided on plunger 30 prevents the fluid F contained within container 28 from passing between the plunger and the inner walls of the container, the fluid will be forced outwardly of the device through delivery tube 36. The amount of fluid passing through the delivery tube is precisely proportional to the travel of container 28 along the internal threads of base 22 as container 28 is rotated by the drive means. Accordingly, by closely controlling the rotation of the container 28, the delivery of the fluid from the device can be precisely and accurately controlled. More specifically, by providing very fine threads on the mating parts and through close control of the drive means or measurement directly from the container 28, high precision and accuracy in the delivery of small or large liquid aliquots can consistently be achieved.

Because the device embodies a minimum number of moving parts and due to the fact that the drive means is external of the unit and easily accessible, the device is highly reliable, readily maintainable and simple to operate.

Forming an important part of the liquid handling apparatus of the invention are transfer means which are operably associated with each of the liquid delivery means of each of the metering and aspirating devices and the liquid reservoirs 14 and 18 carried by carousels 12 and 16. The function of the transfer means of the invention is to controllably transfer liquid between the liquid delivery means of a selected metering and aspirating device and a selected one of the liquid reservoirs carried by the two rotating carousels. In the embodiment of the invention shown in FIG. 1, a second transfer means is provided in the form of elongated conduits 64 which are interconnected via couplers 66 with the liquid delivery means, or conduit 36, of two of the liquid metering devices, namely the devices shown in the right hand portion of FIG. 1. A first transfer means is, in this instance, provided in the form of a conduit 64 which is interconnected with conduit 36 of the remaining one of the liquid metering and aspirating devices by means of a connector 66 and a reservoir selection or transfer mechanism generally designated in FIG. 1 by the numeral 68. Mechanism 68 includes an upstanding column 70 which is rotatably carried by a base 72. Affixed to standard 70 and extending perpendicularly therefrom, is an arm 74 which is adapted to carry a portion of the conduit 64 designated in FIG. 1 by the numeral 64a. Column 70 is carried by base 72 to permit controlled up and down movement.

Another important feature of each of the liquid metering and aspirating subassemblies of the present form of the apparatus of the invention comprises control means for precisely controlling the rotation of container 28 relative to base 22 and for providing an automatic readout of the volume of fluid aspirated or dispensed. It is apparent that the travel of the plunger 30 is directly proportional to the extent of rotation of the container relative to the base. It is equally apparent that the amount of fluid aspirated or dispensed is directly proportional to the degree of travel of the plunger within the container. Accordingly, by controlling the rotation of the container relative to the base by a suitable control means such as a digital control device C, which is fixedly mounted above the container and reads radially extending lines "L" provided on the top of the container, the amount of fluid dispensed can readily be controlled. The calculations of fluid dispensed as well as the instrumentation required to appropriately program and control rotation of the container relative to the base are well understood and will not be discussed in detail herein. However, by way of example, the control means can take the form of an encoder reader of a character well known to those skilled in the art. The control means can also take the form of a digital control device such as an optical or magnetic device which will provide for the precise control of rotation of the container and, therefore, precise control of the fluid dispensing and aspirating operations of the liquid metering and aspirating devices of the invention. As indicated in FIG. 2, the digital control device designated "R" can alternatively be mounted on base 22 and be vertically movable within a slot 69 provided in the base 22. By various mechanical means understood by those skilled in the art, the control device "R" can be moved downwardly as container 28 is threaded into the base thereby causing continuous reading of the read marks B.

When multiple liquid metering an aspirating devices comprise subassemblies of the apparatus of the invention as shown in FIG. 1, each device is provided with appropriate control means such as a digital control device of the character described in the preceding paragraph. These devices when associated with suitable computerized equipment, provide means for controllably aspirating or dispensing precise quantities of liquids from the various cartridges 28 in predetermined sequences and in predetermined volumes. In a manner presently to be described, the control means of the invention further controls, via the first and second transfer means, the dispensing of liquid into, or the withdrawal of liquid from, selected reservoirs 14 and 18 carried by carousels 12 and 16. In this regard, each of the carousels is provided with carousel drive means such as a roller 73 driven by a motor 75 via a shaft 78, or some friction, belt or other means of motion since close control or motion can be achieved by observing the position of the container 28 and not necessarily by motor position.

Figure 5:
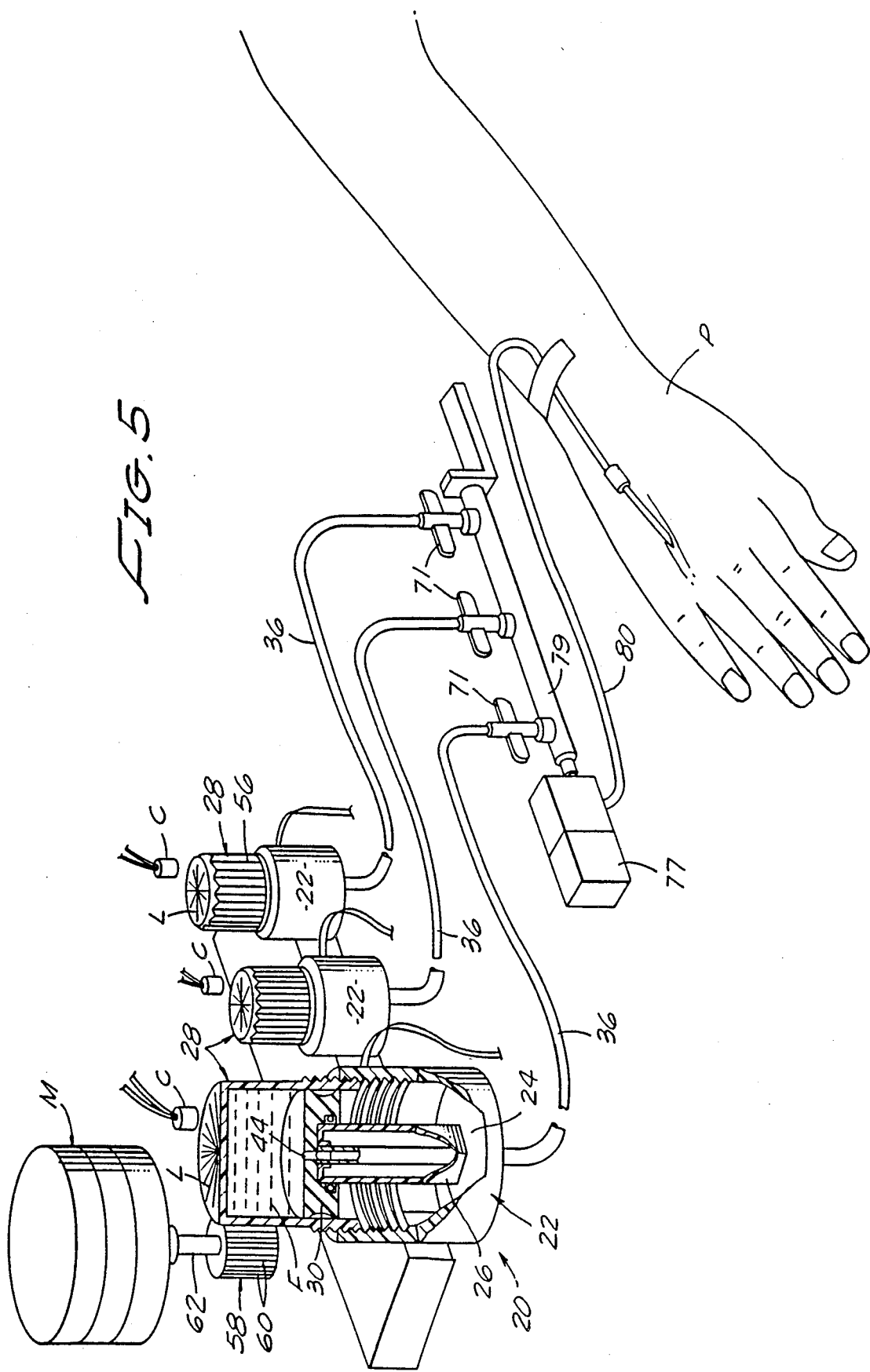
FIG. 5 is a perspective view of another embodiment of the liquid handling apparatus of the invention. Portions of the apparatus shown in FIG. 5 are enlarged, exploded and shown partially in cross section to illustrate the configuration of the liquid metering and aspirating devices of this form of the invention wherein a reader records movement of radial encoded lines provided on the closed end of the liquid cylinders.

Turning now to FIG. 5, an alternate embodiment of the liquid handling apparatus of the present invention is there illustrated. In this form of the invention, the apparatus functions both as an infusion device and as an aspirating device. When used as an infusion device, precise amounts of a desired fluid can be infused into a patient via an access catheter. When used as an aspirating device, precise amounts of blood can be withdrawn from the patient for in vitro analysis. In this latter form of the invention the liquid metering and aspirating devices are of identical construction to that previously described herein and like numerals are used in FIG. 5 to identify like component parts.

With the apparatus of the invention set up in the manner shown in FIG. 5, three liquid metering and aspirating devices are used, each device having a liquid delivery means, or conduit, 36 which is in communication with the interior of liquid containers 28 of the devices. Each of the liquid delivery conduits are operably associated with delivery means, which, in this form of the invention, comprise connectors such as Luhr locks 71 which are interconnected with an elongated liquid manifold, or reservoir, 79 at spaced apart locations. Manifold 79 is in turn interconnected at one end thereof with an access catheter 80 of a character well known to those skilled in the art of the type used for the intravenous supply of fluids to a patient "P" without the use of control valves or other flow control devices. Disposed intermediate manifold 79 and access catheter 80 is an apparatus 77 for measuring blood chemistry. The purpose of this apparatus will be discussed more fully hereinafter.

The liquid metering and aspirating devices of this form of the invention operate in precisely the same manner as previously described herein. Each of the devices includes an externally threaded liquid container 28 which may be a prepackaged disposable reagent container containing various types of reagents or other liquids. As was the case in the previously described embodiment of the invention, motor means M drive each unit and each is controlled by an encoder C which reads radial markings on each container or cartridge 28 to provide precision control of dosage and precise control of time intervals for metering a particular reagent from a given cartridge 28 through delivery means 36 to the reservoir, or manifold, 79. By preprogramming the drive means of the invention a single liquid, or a mixture of several liquids, contained in cartridges 28 can be delivered to manifold 79 and thence to the patient via access catheter 80.

OPERATION

In operating the apparatus of the embodiment of the invention illustrated in FIG. 1, a container 28 in the form of a disposable reagent cartridge is inserted into base 22 of each liquid metering and aspirating device and the square hole provided in the plunger of the device is moved into locking engagement with the hollow stator, or stanchion, 26. Each conduit 36 is then threaded through the center of the square, hollow stator 26 to the exterior of the unit.

Upon rotation of a selected cartridge 28 by the motor M associated therewith, the external threads provided on the cartridge will engage the internal threads provided on the base 22. As the cartridge rotates, the bar code B provided on each cartridge is read by the bar code reader R where reader R is provided with a slot 69 which permits travel in concert with bar code B or where a reader such as reader C (FIG. 1) is provided above container 28 so as to read bars created by splines 56 or like radial markings. In this way, control of motor M and the resultant rotation of each cartridge 28 can be automatically regulated.

The end 64a of conduit 36 of the liquid metering and aspirating device shown in enlarged form in FIG. 1 is then interconnected with the transfer mechanism 68 in the manner previously described. Central column 70 of the transfer mechanism 68 has the ability to move up and down relative to base 72 as well as to rotate through an arc. Accordingly, a liquid sample can be selected, for example, from a reservoir 14 carried by carousel 12 and transferred to a selected reservoir 18 carried by carousel 16 and dispensed together with suitable diluent. It is to be understood that cartridges 28 of each liquid metering and aspirating device can contain various reagents or other liquids. For example, one cartridge 28 might contain a secondary reagent and another cartridge might contain a triggering substance.

As indicated in FIG. 1 liquid from one of the cartridges 28 can be dispensed into a reservoir 14 carried by carousel 12 and a second liquid carried by the adjacent cartridge 28 can be dispensed into the same reservoir as, for example, the reservoir designated by the numeral 18a in FIG. 1. A third liquid can be added to reservoir 18a through use of transfer mechanism 68. For example, by rotating the transfer mechanism 68 so that the end of conduit 64a is over carousel 16 and then by rotating carousel 16 until reservoir 18a comes to rest beneath the free end of conduit portion 64a, liquid contained in the cartridge shown in enlarged form in FIG. 1 can be dispensed into reservoir 18a and mixed with the liquids previously dispensed therein from the remaining two cartridges 28 of the apparatus.

In yet another mode of operation of the apparatus of the invention, the transfer mechanism 68 can be positioned over carousel 12 and a selected reservoir 14 positioned beneath the free end of conduit portion 64a through rotation of carousel 14. The transfer mechanism can then be lowered so that the end of the conduit 64a is immersed into the selected reservoir 18 and fluid can either be dispensed into the reservoir by rotation of cartridge 28 in a first direction, or liquid can be withdrawn therefrom by rotating cartridge 28 in the opposite direction. With this unique arrangement, it is apparent that fluids can be selectively mixed in a given reservoir 18, or, alternatively, can be mixed within the cartridge 28. Because different liquids can be contained in the various reservoirs 18, it is apparent that any number of liquids can be controllably mixed to accomplish any number of desired reactions.

As previously mentioned, transfer mechanism 68 can also be rotated so that the end of conduit portion 64a is above one of the reservoirs 18 carried by carousel 14. In this position, fluid can be dispensed from cartridge 28, shown in enlarged form in FIG. 1, or, alternatively, by lowering the transfer mechanism so that the free end of conduit 64 is immersed in liquid contained in one of the reservoirs 14, liquid can be withdrawn from the reservoir and mixed with liquid contained within the cartridge 28.

With the unique construction described in the preceding paragraphs and by the proper use of pre-programmed digital control devices, any number of liquids can be controllably mixed and transferred among selected reservoirs 14 and 18 carried by carousels 12 and 16 as well as within cartridges 28 carried by the various liquid metering and aspirating devices of the invention. By proper programming of motors M and electrical drive means for driving carousels 12 and 16 in a manner well known to those skilled in the art and through use of appropriate digital devices such as bar code reader R and C, precise, controlled mixing of large numbers of liquids can be automatically and expeditiously accomplished.

In operating the apparatus of the embodiment of the invention illustrated in FIG. 5, a container 28, for example, in the form of a disposable reagent cartridge is inserted into base 22 of each liquid metering and aspirating device and the square hole provided in the plunger of the device is moved into locking engagement with the hollow stator, or stanchion, 26. Each conduit 36 is then threaded through the center of the square, hollow stator 26 to the exterior of the unit.

Upon rotation of a selected cartridge 28 by the motor M associated therewith, the external threads provided on the cartridge will engage the internal threads provided on the base 22. As the cartridge rotates, the radial markings provided on the top of each cartridge is read by the encoder C. In this way, control of motor M and the resultant rotation of each cartridge 28 can be automatically regulated to provide precise control of dosage to the patient via manifold 79.

Reversal of the direction of rotation of ant one of the cartridges 28 will cause blood to be drawn from the patient via the catheter. When the blood reaches the apparatus 77, measurements such as measurement of the blood electrolytes, blood gas analysis and the like can be made. Apparatus 77 can be of several different designs, but the apparatus disclosed in Kater U.S. Pat. No. 4,535,786 is suitable for use in the present application. Reference should be made to this patent for the details of construction and operation of apparatus 77. Once the blood analysis is complete, the blood can be returned to the patient by rotating the selected cartridge 28 in the opposite direction.

Figure 8:
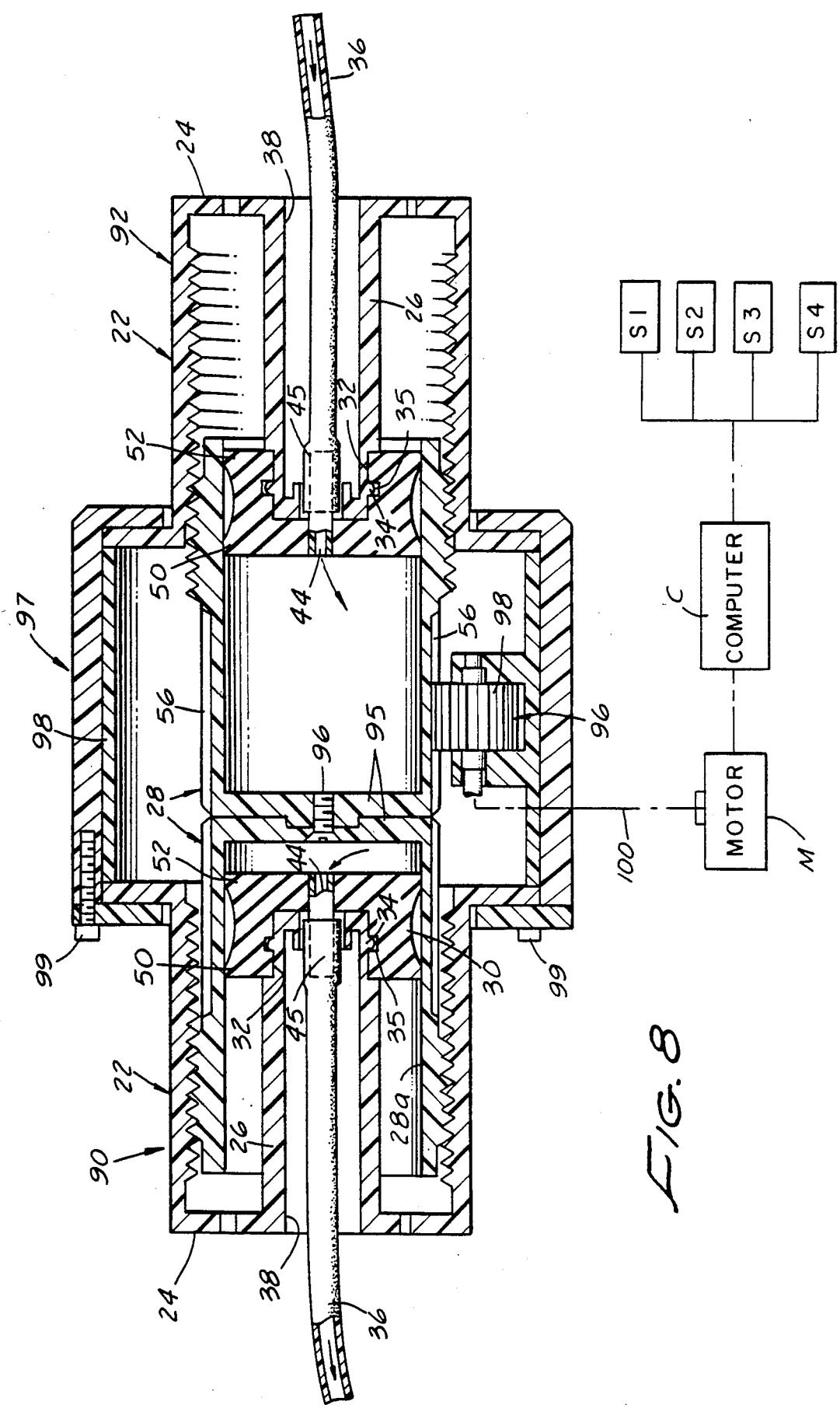
FIG. 8 is an enlarged cross-sectional view similar to FIG. 6 showing movement of the reagent containers to the left.

Referring to the drawings and particularly to FIGS. 6 and 8 of the drawings, another embodiment of the liquid handling apparatus of the present invention is there illustrated. In this form of the invention the apparatus comprises a pair of liquid metering and aspirating devices 90 and 92 which are disposed in a back-to-back relationship and are operably associated with a drive means adapted to simultaneously drive the externally threaded containers of the devices. It is to be noted that the liquid metering and aspirating devices 90 and 92 of this embodiment of the invention are of the same construction as previously described and like numbers are used in FIGS. 6 through 9 to identify like components.

Each of the liquid metering and aspirating devices of this form of the invention comprises an internally threaded hollow base member 22 having a bottom closure wall 24, a rigid stator, or upstanding hollow column, 26 mounted within base member 22 and an externally threaded liquid container 28 adapted to be threadably interconnected with base member 22 upon rotation of container 28 relative to base member 22. Each of the liquid metering and aspirating devices of the invention further includes a liquid delivery means for conducting fluid from the interior of the liquid container 28 to the exterior of the device and a non-rotatable plunger 30 reciprocatable movable a precise axial distance with respect to liquid container 28 upon rotation of the container 28 relative to the base member 22.

The plungers 30 of the liquid metering an aspirating devices each have sealing means adapted to sealably engage the inner wall 28a of the liquid container 28 for preventing leakage of fluid between the plunger and the inner wall of the container upon non-rotatable axial movement of the plunger 30 within the liquid container 28 (FIG. 8). Plunger 30 is also provided with connecting means for operably interconnecting the plunger with the stator 26 for preventing rotation of the plunger relative to the stator. Additionally, the plunger includes releasable locking means for releasably interconnecting the plunger with the stator to prevent relative axial movement therebetween during the aspirating mode of operation of the device.

In the embodiment of the invention shown in the drawings, the connecting means of each liquid metering and aspirating device is provided in the form of a cavity 32 which, as shown n FIG. 8, is generally rectangular in cross-section and is adapted to closely receive the upper end portion of the stator, or upstanding column, 26. The interlocking means in the form of the invention comprises a resiliently deformable locking member 34, such as a molded detent or a thin metal spring or wire, which is receivable within a circumferentially extending groove 35 formed in cavity 32 of plunger 30. As will be discussed in greater detail hereinafter, when container 28 is rotated relative to base 22, the upper portion of stator 26 will be closely received within cavity 32. As this occurs, the resiliently deformable locking member 34 will frictionally engage and securely grip the side walls of stator, or column 26, thereby yieldably resisting relative axial or rotational movement between the plunger 30 and the stator 26.

In each of the liquid metering and aspirating devices of the apparatus, delivery means is provided in the form of a tubular conduit 26 which extends through an aperture 38 formed in bottom wall of base 24. Plunger 30 is provided with a fluid passageway 44 having one end communicating with the interior of the liquid container 28 and the other end communicating with the first, end 45 of conduit 36.

In the present embodiment of the invention, the previously identified sealing means of each liquid dispensing and aspirating device comprises a pair of spaced apart circumferentially extending skirts 50 and 52, the outer edges of which press resiliently against the inner wall 28a of container 28.

The drive means of this form of the invention comprises a multiplicity of splines 56 provided about the periphery of each of the liquid containers. A drive roller 96, also having a multiplicity of splines 98 provided about its periphery, is adapted to mateably engage and controllably drive the pair of reagent containers 28. A motor means M is operably connected with drive roller 96 by a suitable driving connection 100. The details of the operation of the drive and control means of the present form of the invention will be discussed in greater detail in the paragraphs which follow.

As best seen by referring to FIGS. 7, 8 and 9, the top walls 95 of containers 28 are connected by a centrally located, threaded connector 96. Additionally, an external, generally cylindrical framework 97, which includes a cylindrical spacer 98 and threaded connectors 99, interlocks members 22 together so as to maintain them in a spaced apart fixed relationship relative to one another. Drive roller 96 is rotatably mounted within framework 97 in the manner shown in the drawings so as to driveably engage splines 56 provided on containers 28. With this construction, rotation of drive roller 96 in a first direction will cause the interconnected containers to move as a unit in a first direction relative to bases 22, while rotation of roller 96 in a second, opposite direction will cause the interconnected containers to move in an opposite direction. As illustrated in FIGS. 7 and 8, when roller 96 moves in a counter clockwise direction, interconnected containers 28 will rotate in a clockwise direction. This results in fluid being expelled from the left container as viewed in FIG. 8 via conduit 36, while at the same time, fluid is being aspirated into the right container.

The construction described in the preceding paragraphs finds wide application in automotive and aircraft systems and other types of fluid actuated mobile and stationary devices, such as robotic positioning devices. With the device of this embodiment of the invention, fluid preloaded into containers 28, which can be fixed or replaceable, can be directed via conduits 36 to remote locations to activate any type of fluid actuated subsystem such as, for example, a piston/cylinder positioning mechanism of the character used in aircraft piloting surfaces or on machinery such as robodic devices where precision, real time positioning and high reliability is required. Such a subsystem is schematically illustrated in FIG. 8 wherein a computer C controls motor M based upon signals received from remotely located sensors S-1, S-2, S-3, and S-4, which are strategically placed to sense varying load conditions. The computer C interprets data received form the sensors and controls motor M in a manner to appropriately respond to the load conditions within the remotely located subsystems Computer C, as well as the sensors S, are commercially available and their operation and interconnection for a particular end use are well understood by those skilled in the art.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. A liquid handling apparatus comprising:
   (a) first and second operably interconnected liquid metering and aspirating devices each comprising:
      (i) a threaded hollow base member having a bottom closure wall;
      (ii) a rigid stator non-rotatably mounted within said base member;
      (iii) a threaded liquid container adapted to be threadably interconnected with said base member upon rotation of said container relative to said base member, said container having an inner wall and a top closure wall;
      (iv) conduit means for conducting fluid between the interior of said liquid container and the exterior of the device; and
      (v) a non-rotatable plunger reciprocally movable a precise axial distance within said liquid container only upon rotation of said container relative to said base member, said plunger having:
         (1) sealing means adapted to sealable engage said inner wall of said liquid container for preventing leakage of fluid between said plunger and said inner wall upon non-rotatable axial movement of said plunger within said liquid container; and
         (2) connecting means for operably interconnecting said plunger with said stator for preventing rotation of said plunger relative to said stator; and
   (b) drive means for simultaneously rotating said liquid containers of said first and second liquid metering and aspirating devices in a first direction whereby fluid is expelled from said first liquid container of said first liquid metering and aspirating device and fluid is aspirated into said liquid container of said second liquid metering and aspirating device.

2. A liquid handling apparatus as defined in claim 1 in which said drive means simultaneously rotates said liquid containers of said first and second liquid metering and aspirating devices in a second direction whereby fluid is aspirated into said first liquid container of said first liquid metering and aspirating device and fluid is expelled from said liquid container of said second liquid metering and aspirating device.

3. A liquid handling apparatus as defined in claim 1 in which said liquid containers of said first and second liquid metering and aspiration devices are interconnected, each having a plurality of splines provided on the external, peripheral surface thereof.

4. A liquid handling apparatus as defined in claim 3, in which said drive means comprises:
   (a) a drive gear having splines engage able with said splines provided on said liquid containers; and
   (b) a motor for controllably driving said drive gear.

5. A liquid handling apparatus as defined in claim 4 further including a frame interconnected with said base members of said first and second liquid metering and aspiration devices for holding said base members in a spaced apart, fixed location.

6. A liquid handling apparatus as defined in claim 5 in which said motor of said drive means is mounted on said frame.

7. A liquid handling apparatus for use in combination with a fluid actuated device of the character requiring fluid to be alternately supplied to and withdrawn from the device, said apparatus comprising;
   (a) first and second operably interconnected liquid metering and aspirating devices each comprising:
      (i) a threaded hollow base member having a bottom closure wall;
      (ii) a rigid stator non-rotatably mounted within said base member;
      (iii) a threaded liquid container adapted to be threadably interconnected with said base member upon rotation of said container relative to said base member, said container having an inner wall and a top closure wall;
      (iv) conduit means operably interconnected with said fluid actuated device for conducting fluid between the interior of said liquid container and the exterior of the fluid actuated device; and
      (v) a non-rotatable plunger reciprocally movable a precise axial distance within said liquid container only upon rotation of said container relative to said base member, said plunger having:
         (1) sealing means adapted to sealable engage said inner wall of said liquid container for preventing leakage of fluid between said plunger and said inner wall upon non-rotatable axial movement of said plunger within said liquid container; and
         (2) connecting means for operably interconnecting said plunger with said stator for preventing rotation of said plunger relative to said stator.

* * * * *